United States Patent [19]
Thomas et al.

[11] Patent Number: 5,436,375
[45] Date of Patent: Jul. 25, 1995

[54] REACTION OF ISOBUTANE WITH OXYGEN

[75] Inventors: Karen A. Thomas, Houston; Kyle L. Preston, Port Neches, both of Tex.

[73] Assignee: Texaco Chemical Inc., White Plains, N.Y.

[21] Appl. No.: 296,633

[22] Filed: Aug. 26, 1994

[51] Int. Cl.[6] .................... C07C 409/04; C07C 27/10
[52] U.S. Cl. .................. 568/571; 568/568; 568/569; 568/910
[58] Field of Search ............. 568/568, 569, 910, 571

[56] References Cited

U.S. PATENT DOCUMENTS

| | | | |
|---|---|---|---|
| 2,845,461 | 7/1958 | Winkler et al. | 568/910 |
| 4,294,999 | 10/1981 | Grane et al. | 568/910 |
| 4,296,262 | 10/1981 | Grane et al. | 568/910 |
| 4,296,263 | 10/1981 | Grane et al. | 568/910 |
| 4,547,998 | 10/1985 | Sanderson et al. | 568/922 |
| 4,705,903 | 11/1987 | Sanderson et al. | 568/922 |
| 5,093,506 | 3/1992 | Marquis et al. | 568/571 |
| 5,149,885 | 9/1992 | Jubin, Jr. | 568/571 |
| 5,151,530 | 9/1992 | Marquis et al. | 568/571 |
| 5,159,122 | 10/1992 | Sanderson et al. | 568/699 |
| 5,185,480 | 2/1993 | Sanderson et al. | 568/913 |
| 5,243,083 | 9/1993 | Cowley et al. | 568/571 |
| 5,243,091 | 9/1993 | Kruse et al. | 568/697 |

Primary Examiner—Werren B. Lone
Attorney, Agent, or Firm—James L. Bailey; Kenneth R. Priem; Carl G. Ries

[57] ABSTRACT

Tertiary butyl hydroperoxide and tertiary butyl alcohol are prepared from isobutane and oxygen in a vertical reactor by sparging a mixture of isobutane with oxygen to the bottom of the reactor, by charging a reaction mixture recycle stream to the reactor above the sparge point, by centrally charging a downwardly flowing stream of cooled fresh isobutane to the top of the reactor to induce central downflow of the fresh isobutane annular and upflow of the sparged mixture and the recycle stream, by withdrawing a liquid product stream adjacent the top of the reactor, by withdrawing a vapor product stream from the top of the reactor, by condensing entrained liquids in the vapor product, by recycling the condensed liquids and by recovering the liquid product stream.

5 Claims, 2 Drawing Sheets

REACTION OF ISOBUTANE WITH OXYGEN

BACKGROUND OF THE INVENTION

1. Field of the Invention

This invention relates to a process for the non-catalytic production of tertiary butyl hydroperoxide and tertiary butyl alcohol from isobutane and oxygen in a vertical reactor. More particularly, this invention relates to the preparation of tertiary butyl hydroperoxide and tertiary butyl alcohol from isobutane and oxygen in a vertical reactor by sparging a mixture of isobutane with oxygen to the bottom of the reactor, by charging a reaction mixture recycle stream to the reactor above the sparge point, by centrally charging a downwardly flowing stream of cooled fresh isobutane to the top of the reactor to induce central downflow of the fresh isobutane and annular upflow of the sparged mixture and the recycle stream, by withdrawing a liquid product stream adjacent the top of the reactor, by withdrawing a vapor product stream from the top of the reactor, by condensing entrained liquids in the vapor product, by recycling the condensed liquids and by recovering the liquid product stream.

2. Prior Art

It is known to non-catalytically react isobutane with oxygen in the liquid phase in order to provide a reaction product comprising a mixture of tertiary butyl hydroperoxide with tertiary butyl alcohol as illustrated, for example, by Winkler et al. U.S. Pat. No. 2,845,461.

A plural stage process for the production of tertiary butyl alcohol from isobutane is disclosed in copending Sheu et al. U S patent application Ser. No. 08/288,842, filed Aug. 11, 1994, and entitled "Production of Tertiary Butyl Alcohol".

It is known to react isobutane with oxygen in the presence of a peroxidation catalyst in order to provide a reaction product comprising tertiary butyl alcohol and residual tertiary butyl hydroperoxide as shown, for example, by Grane et al. U.S. Pat. No. 4,294,999, Grane et al. U.S. Pat. No. 4,296,262 and Worrell U.S. Pat. No. 4,296,263.

It is known to prepare tertiary butyl alcohol by the catalyzed decomposition of tertiary butyl hydroperoxide as shown, for example, by Sanderson et al. U.S. Pat. No. 4,547,598.

It is known to purify tertiary butyl alcohol by the catalytic decomposition of residual quantities of tertiary butyl hydroperoxide contained therein using a catalyst, as shown, for example, by Sanderson et al. U.S. Pat. No. 4,705,903, Sanderson et al. U.S. Pat. No. 5,159,122, and Sanderson et al. U.S. Pat. No. 5,185,480.

It is known to use tertiary butyl hydroperoxide prepared by the oxidation of isobutane, as a feedstock, together with propylene for an epoxidation reaction process wherein the propylene and tertiary butyl hydroperoxide are converted to propylene oxide and tertiary butyl alcohol as shown, for example, by Marquis et al. U.S. Pat. No. 5,093,506 and Marquis et al. U.S. Pat. No. 5,151,530.

It is known to use tertiary butyl alcohol obtained by the oxidation of isobutane as a feedstock, together with methanol as a feedstock, for an etherification reaction process wherein the tertiary butyl alcohol and methanol are reacted to form methyl tertiary butyl ether. See, for example, Kruse et al. U.S. Pat. No. 5,243,091.

SUMMARY OF THE INVENTION

In accordance with the present invention, a process for the non-catalytic production of tertiary butyl hydroperoxide and tertiary butyl alcohol from isobutane and oxygen in a vertical reactor is provided which comprises the steps of:

sparging a mixture of isobutane with oxygen to the bottom of the reactor, charging a reflux stream of condensed reactor vapors to the reactor above the sparge point, centrally charging a downwardly flowing stream of cooled fresh isobutane adjacent the top of the reactor and below the liquid level to induce central downflow of the fresh isobutane and annular upflow of the sparged mixture and the reflux stream, withdrawing a liquid product stream adjacent the top of the reactor, withdrawing a vapor product stream comprising isobutane from the top of the reactor, condensing part of the overhead vapor, recycling the condensed stream to near the bottom of the reactor, recycling the non-condensed vapors through a compressor and into the bottom of the reactor, and recovering the liquid product stream, recovering the liquid product stream.

In accordance with a preferred embodiment of the present invention, a process for the non-catalytic production of tertiary butyl hydroperoxide and tertiary butyl alcohol from isobutane in a vertical reactor having a length to diameter ratio of at least 1.1 is provided which comprises the steps of:

establishing reaction conditions within said reactor including a temperature within the range of about 120° to about 165° C. and a pressure within the range of about 380 to about 600 psig, sparging a mixture of isobutane with oxygen into said reactor adjacent the bottom thereof, charging a reaction mixture recycle stream into said reactor adjacent the bottom thereof and above the sparging point for the said mixture of isobutane with oxygen, centrally charging a fresh isobutane charge stream having a charge stream temperature of about 10° to about 55° C. to said reactor adjacent the top thereof in a downwardly flowing direction to induce central downflow of said fresh isobutane in said reactor and to thereby induce annular upflow of said sparged mixture and said reaction mixture recycle stream, withdrawing a liquid product stream adjacent the top of said reactor comprising isobutane, tertiary butyl hydroperoxide, tertiary butyl alcohol and oxygenated hydrocarbon by-products, withdrawing a vapor product stream from the top of said reactor comprising isobutane and entrained normally liquid reaction products, cooling said vapor product to condense normal liquid reaction product components thereof, recycling said condensed products to said reactor as said reaction mixture recycle stream, recycling uncondensed components of said product vapor stream, comprising isobutane to said reactor in admixture with added oxygen as said sparge mixture, and recovering said liquid product stream.

In accordance with the present invention, isobutane is reacted with oxygen in a vertical reactor having a length to diameter ratio of at least 1.1, and preferably a ratio of about 1.1 to 3. The sparged mixture of isobutane and oxygen is peripherally charged adjacent the bottom of the vertical reactor in an upwardly flowing direction and mixes with and is diluted by the reaction mixture recycle stream and is also mixed with and be further diluted adjacent the bottom of the vertical reactor by the downwardly centrally flowing stream of cooled isobutane. This is accomplished because the isobutane charge stream is significantly cooler than the circulating reaction mixture. This stream, being initially cooler and denser than the reaction mixture will flow or sink towards the bottom of the vertical reactor and the displaced liquid will flow upwardly and annularly of the downwardly flowing stream and a convection current will be established. This, in turn, promotes enhanced mixing of reaction mixture components adjacent the bottom of the vertical reactor. Also, introduction of the cooled isobutane feed stream into the vertical reactor below an annular draw-off tray for the liquid reaction product will diminish the likelihood of a break-through of unreacted oxygen into the vapor space at the top of the tower and thus further diminish the likelihood of spontaneous combustion of oxygen and hydrocarbons in the vapor space.

DESCRIPTION OF THE PROCESS OF THE PRESENT INVENTION

In accordance with the present invention, the reaction of isobutane with oxygen is conducted on a non-catalytic basis for a number of reasons. An enhanced amount of tertiary butyl hydroperoxide is formed which can be used in the manufacture of propylene oxide whereas when a catalyst is used the production of tertiary butyl hydroperoxide is limited. Also, if a catalyst is present, the tertiary butyl hydroperoxide will be contaminated with a trace quantity of soluble metals which are deleterious in a propylene oxidation process.

The reaction of isobutane with oxygen is conducted in accordance with the present invention in the manner described below. Thus, liquid isobutane is charged to an oxidation reactor together with oxygen and oxidation reaction conditions are established therein including, for example, a temperature of about 120° to about 165° C. and a pressure of about 380 to about 600 psig in order to non-catalytically convert a portion of the isobutane to oxidation products including tertiary butyl alcohol, tertiary butyl hydroperoxide and minor mounts of oxygen-containing by-products including ditertiary butyl peroxide, methanol, methyl formate, acetone and water. The thus-formed primary liquid reaction mixture will typically comprise about 10 to about 25 wt. % of tertiary butyl hydroperoxide, about 13 to about 20 wt. % of tertiary butyl alcohol, about 50 to about 75 wt. % of unreacted isobutane and about 2 to about 5 wt. % of oxygen-containing impurities.

In accordance with the preferred embodiment of the present invention, a process for the non-catalytic production of tertiary butyl hydroperoxide and tertiary butyl alcohol from isobutane in a vertical reactor having a length to diameter ratio of from about 1.1 to about 3 to 1 is provided which comprises the steps of:

establishing reaction conditions within the reactor including a temperature within the range of about 120° to about 165° C. and a pressure within the range of about 380 to about 600 psig, peripherally sparging about 200 to about 400 parts per hour of a mixture comprising oxygen and isobutane into the reactor adjacent the bottom thereof, the mixture containing 5 to about 15 parts of oxygen per 100 parts of isobutane, charging about 150 to about 250 parts per hour of a reaction mixture recycle stream into the reactor adjacent the bottom thereof and above the sparging point for the mixture of isobutane with oxygen, centrally charging about 100 parts per hour of an isobutane charge stream having a charge stream temperature of about 10° to about 55° C. to the reactor adjacent the top thereof in a downwardly flowing direction to induce central downflow of the fresh isobutane in the reactor and to thereby induce annular upflow of the sparged mixture and the reaction mixture recycle stream, withdrawing about 80 to about 120 parts per hour of a liquid product stream adjacent the top of the reactor comprising isobutane, tertiary butyl hydroperoxide, tertiary butyl alcohol and oxygenated hydrocarbon by-products, withdrawing about 200 to about 400 parts per hour of a vapor product stream from the top of the reactor comprising isobutane and entrained normally liquid reaction products, cooling the vapor product to condense normal liquid reaction product components thereof, recycling the condensed products to the reactor as the reaction mixture recycle stream, recycling uncondensed components of the product vapor stream comprising isobutane to the reactor in admixture with added oxygen as the sparge mixture, and recovering the liquid product stream.

The liquid product stream will normally comprises about 10 to about 25 wt. % of tertiary butyl hydroperoxide, about 13 to about 20 wt. % of tertiary butyl alcohol, about 50 to about 750 wt. % of unreacted isobutane and about 2 to about 5 wt. % of oxygen-containing impurities including ditertiary butyl peroxide, methanol, methyl formate, acetone and water.

In accordance with the preferred embodiment of the present invention, the liquid product stream is charged to a distillation zone and separated therein into a lower boiling isobutane fraction and a higher boiling fraction comprising tertiary butyl hydroperoxide, tertiary butyl alcohol and oxygenated hydrocarbon by-products, and the lighter isobutane fraction is cooled to a temperature of about 10° to about 55° C. and recycled to the reactor as the fresh isobutane charge stream.

The primary liquid reaction product is separated in any suitable manner (e.g., by distillation) so as to provide a first lighter isobutane recycle distillation fraction and a first heavier liquid distillation fraction substantially free from isobutane comprising about 40 to about 55 wt. % of tertiary butyl hydroperoxide, about 45 to 50 wt. % of tertiary butyl alcohol and about 3 to about 5 wt. % of oxygen-containing impurities.

BRIEF DESCRIPTION OF THE DRAWING

In the drawing:

Turning now to FIG. 1 of the drawing, there is schematically shown a vertically mounted oxidation reactor 10 having a length to diameter ratio of least about 1.1 to which a mixture of isobutane with oxygen is continuously sparged by sparge lines 14 and 16 adjacent to the bottom thereof.

A reaction mixture reflux stream is continuously charged to the reactor 10 by line 20 at an injection point adjacent the bottom of the reactor 10 and above the point at which the sparge lines 14 and 16 enter the reactor. Isobutane is centrally continuously charged to reactor 10 in a downwardly flowing direction by an isobutane charge line 12 near the upper liquid level.

Reaction conditions are established within the reactor 10, including a temperature within the range of about 120° to about 165° C. and a pressure within the range of about 380 to about 600 psig.

A liquid product stream is continuously withdrawn from reactor 10 by a line 22 adjacent the top thereof. A vapor product stream comprising isobutane is continuously withdrawn from the top of the reactor 10 by a line 26.

Figure 1:
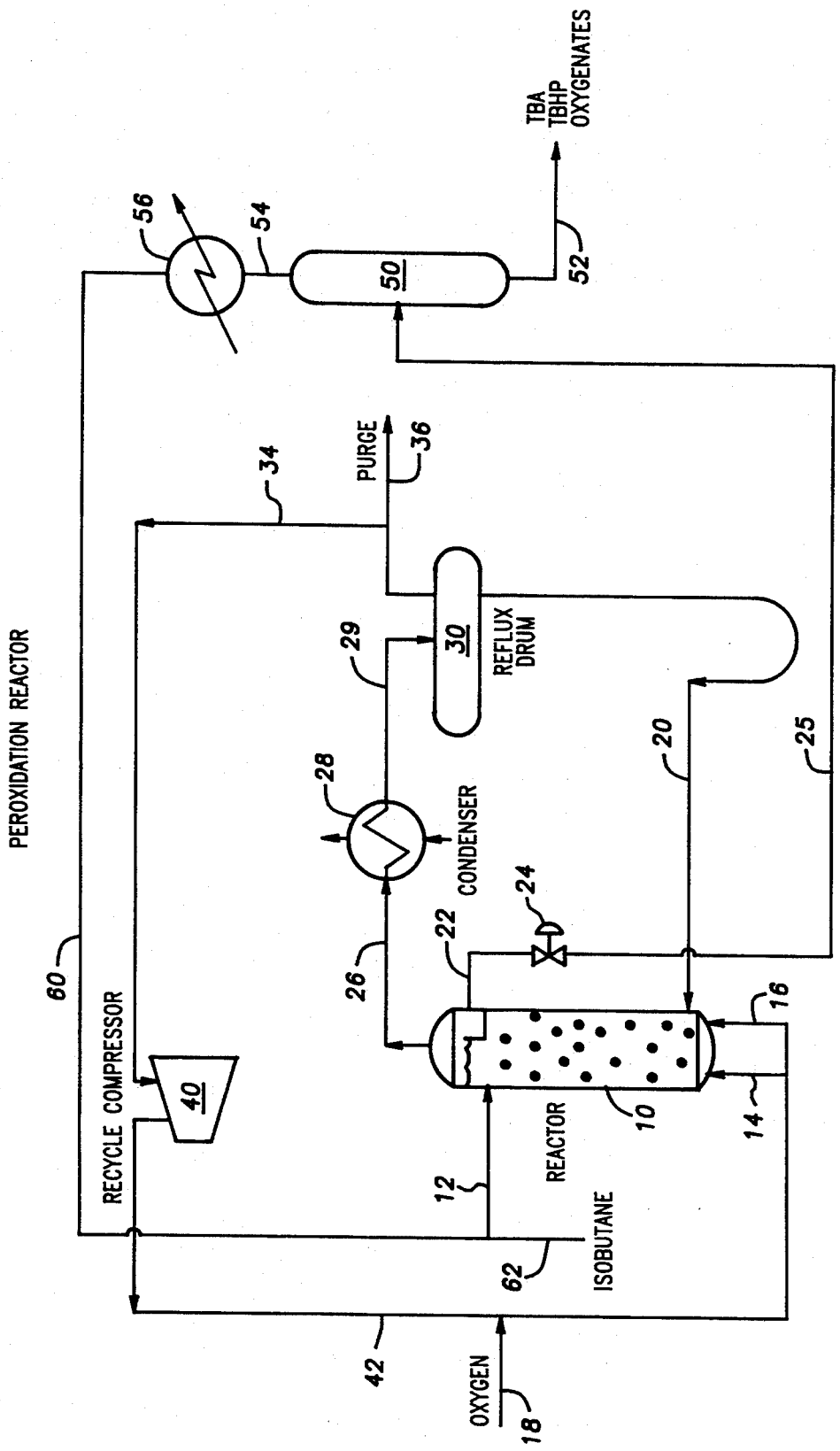
FIG. 1 is a schematic flow sheet illustrating a preferred method for practicing the process of the present invention.
Figure 4:
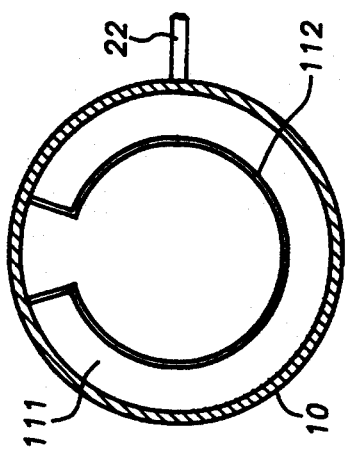
FIG. 4 is a cross-sectional view taken along the lines 4—4 of FIG. 2.
Figure 3:
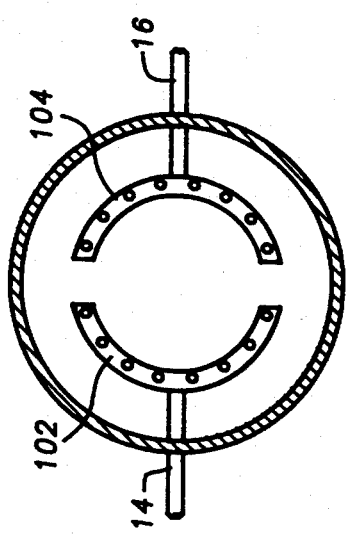
FIG. 3 is a cross-sectional view taken along the lines 3—3 of FIG. 2.
Figure 2:
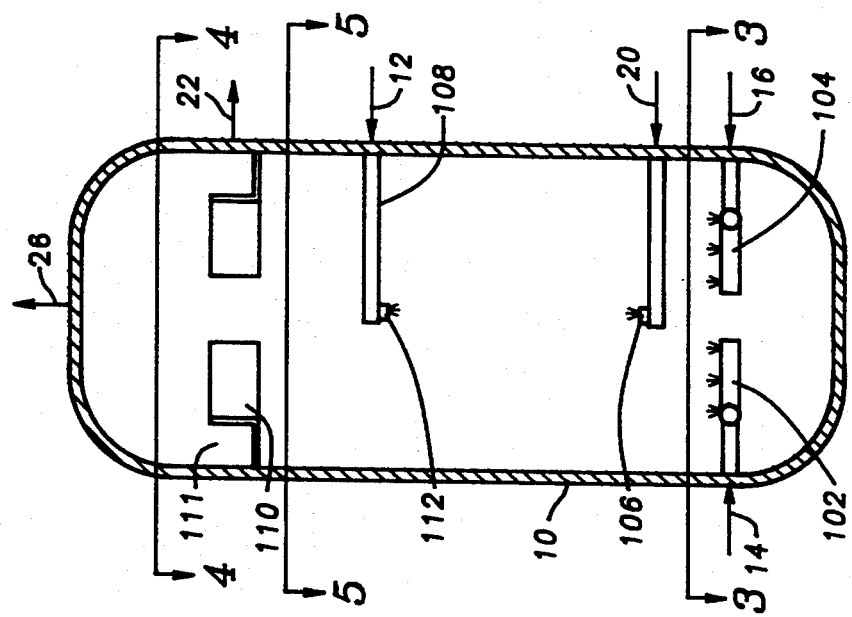
FIG. 2 is a plan view, in section, of the reactor shown in FIG. 1.

With reference to FIGS. 2 and 3 of the drawings, it will be noted that the mixture of oxygen and butane that is charged to reactor 10 is charged by sparge lines 14 and 16 that are connected with corresponding semi-circular shaped spargers 102 and 104 so that the mixture is charged peripherally of the reactor 10 in an upwardly flowing direction.

With further reference to FIG. 2 it will be noted that the reaction mixture recycle stream is charged to reactor 10 by line 20 and injected upwardly into reactor 10 by nozzle 106.

Figure 5:
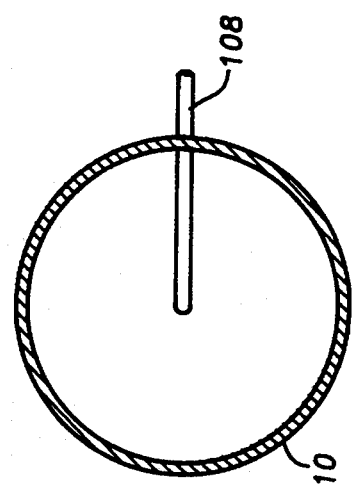
FIG. 5 is a cross-sectional view taken along the lines 5—5 of FIG. 2.

With additional reference to FIG. 2 and to FIG. 5, it will be noted that the cooled isobutane is charged to reactor 10 by line 12 and injected into reactor 10 by a downwardly facing isobutane discharge nozzle 112.

With this arrangement, the cooled isobutane, being denser, and because of the direction at which it is introduced will continuously flow, or "sink" towards the bottom of the reactor 10 where it will meet and mix with the upwardly flowing warmer reaction mixture recycle stream and with the upwardly flowing oxygen-isobutane mixture that is peripherally introduced through spargers 102 and 104.

As a consequence, a convection current is established and maintained within reactor 10 which is defined by the downwardly flowing stream of cooled isobutane and the peripherally, or annularly upwardly flowing stream of recycled reaction mixture, oxygen and isobutane.

A portion of the reaction mixture continuously flows from the convection current to the top of the reactor 10 where the gaseous components of the reaction mixture continuously exit through the top of the reactor 10 by vapor product streamline 26.

An annular liquid draw-off tray 110 defining an annular collecting baffle 111 is mounted in the reactor 10 adjacent to the top thereof, and the degassed liquid reaction mixture components flow continuously across the baffle 111 into the collecting tray 110 and thence from the reactor 10 through liquid product stream drawoff line 22.

The gaseous reaction components that are discharged by vapor product stream line 26, are passed through a condenser 28 where they are partially liquified and then by line 29 to a reflux drum 30. The condensed liquid components of the reaction mixture are returned to the reactor 10 by reaction mixture recycle line 20 in the described manner. The remaining vapors, mostly vaporized isobutane, are withdrawn from the reflux drum 30 by line 34. A minor portion of the stream 34, e.g., from about 5 to about 10 wt. % is purged from the system by purge line 36. The balance of the stream 34 is charged to a recycle compressor 40 where it is repressured to reactor pressure. The repressured stream 42 is directed to sparge lines 14 and 16. Fresh oxygen is mixed with the stream 42, being charged by line 18 in an amount such that the resultant mixture contains about 3 to 10 mol % of oxygen.

The liquid product stream withdrawn from reactor 10 by way of annular draw off tray 110 is discharged by liquid product line 22 that leads to pressure reduction valve 24 where the stream is reduced to substantially atmospheric pressure. The depressured product stream is discharged from valve 24 by a line 25 leading to a distillation zone 50 that may comprise one or a plurality of distillation towers, preferably a single atmospheric tower, where it is fractionated to provide a lower boiling isobutane fraction that is discharged by line 54 and a higher boiling fraction discharged by line 52; the higher boiling fraction comprising, for example, about 40 to 55 wt. % of tertiary butyl alcohol, about 35 to about 45 wt. % of tertiary butyl hydroperoxide and about 3 to 5 wt. % of oxygenates (i.e., oxygen-containing compounds such as acetone, methyl formate, methanol, ditertiary butyl peroxide, water, etc.).

The isobutane fraction 54 is charged to a heat exchanger 56 where it is cooled to a suitable temperature (e.g., a temperature of about 10° to about 55° C.) and it is then charged by line 60 to isobutane charge line 12. Fresh isobutane, as needed, is charged to line 12 by line 62.

EXAMPLES

By way of example, reaction conditions comprising a temperature of about 145° C. and a pressure of about 525 psia are established in reactor 10. A mixture of butane with oxygen containing about 2 parts of oxygen per 100 parts of isobutane is charged to reactor 10 by sparge lines 14 and 16. In a representative run, an isobutane conversion of about 51% is achieved with a selectivity to tertiary butyl alcohol of about 51%, a selectivity to tertiary butyl hydroperoxide of about 36 wt. % a selectivity to acetone of about 5.6 wt. %, a selectivity to ditertiary butyl peroxide of about 0.6 wt. %, a selectivity to isopropyl alcohol of about 0.4 wt. % and a selectivity to methanol of about 2.5 wt. %.

The liquid product stream in the representative run contains, on the basis of parts by weight per 100 parts of product, about 66.2 parts of isobutane, about 16.5 parts of tertiary butyl alcohol, about 14.6 parts of tertiary butyl hydroperoxide, about 1.1 parts of acetone, about 0.1 part of isopropyl alcohol, about 0.4 part of ditertiary butyl peroxide and about 0.5 part of methanol.

Having thus described our invention, what is claimed is:

1. A process for the non-catalytic production of tertiary butyl hydroperoxide and tertiary butyl alcohol from isobutane and oxygen in a vertical reactor which comprises the steps of:

sparging a mixture of isobutane with oxygen to the bottom of the reactor, charging a reaction mixture recycle stream to the reactor above the sparge point, centrally charging a downwardly flowing stream of cooled fresh isobutane to the top of the reactor to induce central downflow of the fresh isobutane and annular upflow of the sparged mixture and said recycle stream, withdrawing a liquid product stream adjacent the top of the reactor, withdrawing a vapor product stream comprising isobutane from the top of the reactor, partially condensing the vapor stream, recycling the condensed isobutane to the top of the reactor, and recovering the liquid product stream.

2. A process for the non-catalytic production of tertiary butyl hydroperoxide and tertiary butyl alcohol from isobutane in a vertical reactor having a length to diameter ratio of at least about 1.1 which comprises the steps of:

establishing reaction conditions within said reactor including a temperature within the range of about 120° to about 165° C. and a pressure within the range of about 380 to about 600 psig, sparging a mixture of isobutane with oxygen into said reactor adjacent the bottom thereof, charging a reaction mixture recycle stream into said reactor adjacent the bottom thereof and above the sparging point for the said mixture of isobutane with oxygen, centrally charging a fresh isobutane charge stream having a charge stream temperature of about 10° to about 55° C. to said reactor adjacent the top thereof in a downwardly flowing direction to induce central downflow of said fresh isobutane in said reactor and to thereby induce annular upflow of said sparged mixture and said reaction mixture recycle stream, withdrawing a liquid product stream adjacent the top of said reactor comprising isobutane, tertiary butyl hydroperoxide, tertiary butyl alcohol and oxygenated hydrocarbon by-products, withdrawing a vapor product stream from the top of said reactor comprising isobutane and entrained normally liquid reaction products, cooling said vapor product to condense normal liquid reaction product components thereof, recycling said condensed products to said reactor as said reaction mixture reflux stream, recycling uncondensed components of said product vapor stream, comprising isobutane to said reactor in admixture with added oxygen as said sparge mixture, and recovering said liquid product stream.

3. A method as in claim 2 wherein said liquid product stream is charged to a distillation zone and separated therein into a lower boiling isobutane fraction and a higher boiling fraction comprising tertiary butyl hydroperoxide, tertiary butyl alcohol and oxygenated hydrocarbon by-products, and wherein said lighter isobutane fraction is cooled to a temperature of about 10° to about 55° C. and recycled to said reactor as said fresh isobutane charge stream.

4. A process for the non-catalytic production of tertiary butyl hydroperoxide and tertiary butyl alcohol from isobutane in a vertical reactor having a length to diameter ratio of from about 1.1 to about 3 to 1 which comprises the steps of:

establishing reaction conditions within said reactor including a temperature within the range of about 120° to about 165° C. and a pressure within the range of about 380 to about 600 psig, peripherally sparging about 200 to about 400 parts per hour of a mixture comprising oxygen and isobutane into said reactor adjacent the bottom thereof, said mixture containing 5 to about 15 parts of oxygen per 100 parts of isobutane, charging about 150 to about 250 parts per hour of a reaction mixture recycle stream into said reactor adjacent the bottom thereof and above the sparging point for the said mixture of isobutane with oxygen, centrally charging about 100 parts per hour of a fresh isobutane charge stream having a charge stream temperature of about 10° to about 55° C. to said reactor adjacent the top thereof in a downwardly flowing direction to induce central downflow of said fresh isobutane in said reactor and to thereby induce annular upflow of said sparged mixture and said reaction mixture recycle stream, withdrawing about 80 to about 120 parts per hour of a liquid product stream adjacent the top of said reactor comprising isobutane, tertiary butyl hydroperoxide, tertiary butyl alcohol and oxygenated hydrocarbon by-products, withdrawing about 200 to about 400 parts per hour of a vapor product stream from the top of said reactor comprising isobutane and entrained normally liquid reaction products, cooling said vapor product to condense normal liquid reaction product components thereof, recycling said condensed products to said reactor as said reaction mixture recycle stream, recycling uncondensed components of said product vapor stream comprising isobutane to said reactor in admixture with added oxygen as said sparge mixture, and recovering said liquid product stream.

5. A method as in claim 4 wherein the liquid product stream comprises about 10 to about 25 wt. % of tertiary butyl hydroperoxide, about 13 to about 20 wt. % of tertiary butyl alcohol, about 50 to about 75 wt. % of unreacted isobutane and about 2 to about 5 wt. % of oxygen-containing impurities including ditertiary butyl peroxide, methanol, methyl formate, acetone and water, wherein said liquid product stream is charged to a distillation zone and separated therein into a lower boiling isobutane fraction and a higher boiling fraction comprising tertiary butyl hydroperoxide, tertiary butyl alcohol and oxygenated hydrocarbon by-products, and wherein said lighter isobutane fraction is cooled to a temperature of about 10° to about 55° C. and recycled to said reactor as said fresh isobutane charge stream.

* * * * *